US006224827B1

(12) United States Patent
Lembke

(10) Patent No.: US 6,224,827 B1
(45) Date of Patent: *May 1, 2001

(54) DISINFECTANT

(75) Inventor: Fritz Lembke, Erligheim (DE)

(73) Assignee: Tetra Laval Holdings & Finance S.A., Pully (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,003

(22) PCT Filed: Mar. 29, 1996

(86) PCT No.: PCT/IB96/00263

§ 371 Date: Sep. 29, 1997

§ 102(e) Date: Sep. 29, 1997

(87) PCT Pub. No.: WO96/29868

PCT Pub. Date: Oct. 3, 1996

(30) Foreign Application Priority Data

Mar. 31, 1995 (SE) .................................................. 9501178

(51) Int. Cl.$^7$ ................................ A61L 2/18; B08B 9/00; C01B 15/01
(52) U.S. Cl. .................................. 422/28; 422/7; 134/2; 134/22.14; 252/186.43; 510/371
(58) Field of Search .......................... 422/7, 28; 424/616, 424/62, 405; 252/186.43; 510/131, 371, 372; 134/2, 22.14; 514/714, 724

(56) References Cited

U.S. PATENT DOCUMENTS

| 4,233,242 | * | 11/1980 | Nagato et al. ............... 564/249 |
| 4,647,458 | * | 3/1987 | Ueno et al. .................. 424/128 |
| 4,900,721 | * | 2/1990 | Bansemir et al. .............. 514/25 |
| 5,447,684 | * | 9/1995 | Williams ..................... 422/20 |
| 6,106,774 | * | 8/2000 | Monticello et al. ............ 422/28 |

FOREIGN PATENT DOCUMENTS

| 0 016 319 | 10/1980 | (EP) . |
| 0 404 015 | 12/1990 | (EP) . |
| 545288 | 5/1942 | (GB) . |
| 936 677 | 9/1963 | (GB) . |
| 639 824 | 12/1983 | (SE) . |
| WO 84/01894 | 5/1984 | (WO) . |
| 94 00157 | 1/1994 | (WO) . |

OTHER PUBLICATIONS

Derwent Abstract Accession No. 84–049828/198409 entitled!"Hand and Skin–disinfectant aq. compsn.—contg. ethanol and or propan–2– or –1–o1, hydrogen peroxide, surfactant and higher satd. aliphatic alcohol", (1984).*

Derwent Abstract Accession No. 80–58939C entitled: "Aq. sporicidal skin and hand disinfectant compsn.—contains hydrogen peroxide in addn. to ethanol and propanol.", (1980).*

S.S. Block, "Disinfection, Sterilization, and Preservation" 1991, Lea & Febiger, Philadelphia, US, Chapter 11, E.L. Larson et al., 'Alcohols' pp. 191–203; Chapter 22, A.D. Russell 'Chemical Sporicidal and Sporostatic Agents', pp. 365–376.

Chemical Abstracts, vol. 79, No. 25, Dec. 1973, Columbus, Ohio, H.P. Warner et al., "Destruction of spores in alcohol by peracetic acid", Zentralbl.Bakteriol., Parasitenic., Infektion SKR. HGY, Abt.1:ORIG., Reihe B, vol. 157, No. 4, 1973, pp. 387–391.

Patent Abstracts of Japan, vol. 18, No. 58 (C–1159), Jan. 31, 1994, JP A 05 276911 (Taiyo Kagaku), Oct. 26, 1993.

Database WPI Section Ch, Week 8409, Derwent Pubications Ltd., London, GB; Class D21, AN 84–049828, DD A 203 685 (Veb LeunaOWerk Ulricht), Nov. 2, 1983.

Patent Abstracts of Japan, vol. 15, No. 398 (C–0874), Oct. 9, 1991.

* cited by examiner

Primary Examiner—Joseph D. Anthony

(74) Attorney, Agent, or Firm—Burns, Doane, Swecker & Mathis, L.L.P.

(57) ABSTRACT

The invention relates to a water-free alcohol disinfectant capable of destroying spores. Preferably, the disinfectant also contains an additional chemical sterilization agent, e.g., hydrogen peroxide, in very low concentrations within the range of between 0.5 and 3.0 percent of the weight of the alcohol solution. The disinfectant is usable in industrial contexts for bacteriological cleaning of surfaces, for example, inner walls in pipelines, conduits, reaction vessels, and other process equipment, without corroding or chemically attacking the material in such surfaces.

4 Claims, No Drawings

US 6,224,827 B1

DISINFECTANT

This application is a 371 of PCT/IB96/00263 filed on Mar. 29, 1996.

TECHNICAL FIELD

The present invention relates to a disinfectant containing a solution of alcohol. The invention also relates to a method of producing the disinfectant, and use of an alcohol solution containing hydrogen peroxide in a quantity of between 0.3 and 3.0 per cent for destroying spores and similar micro-organisms.

BACKGROUND ART

Alcohol disinfectants are known from, for example, EP-A-O 016 319 which describes such an agent for cleaning wounds and similar practical applications. The prior art disinfectant contains a solution of alcohol to which has been added, for purposes of stabilisation, hydrogen peroxide in an amount of between 0.05 and 1 per cent of the weight of the alcohol solution. According to EP-A-O 016 319, it is possible, by means of this addition of hydrogen peroxide, to prevent the uncontrolled growth of spores and the like unintentionally introduced into the disinfectant. A disinfectant similar to that described above is also known from EP-A-O 252 278 which proposes, also for purposes of stabilisation, the addition of hydrogen peroxide so as to prevent the uncontrolled growth of spores and similar micro-organisms and thereby stabilise the alcohol disinfectant.

In addition to wound treatment and skin cleaning purposes, disinfectants are also employed in industrial contexts for destroying undesired (pathogenic) bacteria and other harmful micro-organisms. In, for example, the food and pharmaceuticals industries, extremely high demands on hygiene are often placed on the produced product, partly in order that the product can be consumed at all, and partly to enable it to be packed and stored without the risk of being destroyed during its storage life as a result of decomposition reactions occasioned by micro-organisms and/or the uninhibited/uncontrolled growth of harmful micro-organisms which may unintentionally accompany the product into its package.

In order to satisfy the demands on product hygiene, it is therefore not least important that the equipment which is used for producing and packaging the product be carefully monitored and controlled and, if necessary or as a preventive measure, be regularly cleaned and disinfected so as to eliminate the presence of harmful micro-organisms in the immediate vicinity of the product. It is of particular importance that such surfaces (for example pipelines, conduits and the like) which the product flows in direct contact with, or otherwise comes into direct contact with during the producing and packing processes are kept hygienically clean and free of micro-organisms which risk harming the product. This naturally also applies to the package and the material from which the package is produced.

For disinfecting and cleaning equipment employed in industrial processes of the type described above, it is known in the art to use solutions of alcohol, such as ethanol and/or propanol. These known agents are active against such micro-organisms as vegetative bacteria, fungi and viruses which may therefore readily be eliminated, but are incapable of combating spores.

Another known disinfectant and cleaning agent for industrial applications is based on chemicals such as peracetic acid, hydrogen peroxide, formaldehyde and glutaraldehyde which are all highly active against not only micro-organisms such as vegetative bacteria, fungi and viruses, but also against spores which may thus readily be eliminated by treatment with these known agents. One problem however is that the these sporicidal agents are highly corrosive and, as a result, also attack and destroy the material, for example stainless steel, plastic, rubber etc., employed in conventional process equipment.

There is thus a need in the art for a disinfectant for industrial use which may efficiently be employed for eliminating micro-organisms, including spores, but which at the same time does not attack and destroy the material, for example non-stainless steel, plastic, rubber etc., in those surfaces from which the micro-organisms are to be eliminated.

OBJECT OF THE INVENTION

One object of the present invention is therefore to realise a disinfectant of the type described by way of introduction which makes for an efficient destruction of undesired micro-organisms, including spores, without chemically attacking the material in those surfaces from which the micro-organisms are to be eliminated.

SOLUTION

This object is attained according to the present invention in that a disinfectant of the type described by way of introduction has been given the characterising feature that the alcohol solution employed is practically water-free.

The term "practically water-free" used in this description and in the appended Claims is here taken to signify an alcohol solution which, while not being completely free of water, contains such a slight quantity of water as it possibly can in order that the object according to the invention be attained. It will be obvious to the skilled reader of this specification that absolutely water-free alcohol solutions seldom exist in practice, since such alcohol solutions are—primarily for technical and economical reasons—difficult or economically indefensible to produce, given the applications for which such alcohol solutions are often intended. Consequently, the expression "practically water-free" in this context implies an alcohol solution which has so little water as is warranted for both production-engineering and economical reasons without jeopardising the object according to the present invention. In order further to clarify and concretise the implications of this expression, it should be added that alcohol solutions of different alcohols contain, or may contain, different quantities of water without departing from the spirit and scope of the inventive concept as herein disclosed. For example, an alcohol solution of ethanol may contain water in quantities of up to approx. 4 per cent, i.e. be a 96 per cent ethanol solution, while an alcohol solution containing propanol (n-propanol and/or isopropanol) may contain water in quantities corresponding to approx. 30 per cent of the weight of the alcohol solution, i.e. be a 70 per cent propanol solution.

The disinfectant according to the invention which is, like the prior art disinfectants according to the above disclosed publications EP-A-O 016 319 and EP-A-O 252 278, based on an alcohol solution thus differs from these prior art disinfectants in that the alcohol solution employed is to contain a reduced quantity of water or be practically water-free in the meaning and scope as apparent from the foregoing discussion.

According to the invention, it has surprisingly proved that a disinfectant which is based on an alcohol solution which is practically water-free makes for efficient destruction of micro-organisms, not only of the type such as vegetative bacteria, fungi and viruses, but also of spores, which have previously proved to be difficult or impossible to eliminate using prior art alcohol-based disinfectants.

The disinfectant according to the present invention has further proved to be an efficient cleaning agent in industrial applications for eliminating such micro-organisms, including spores, from the inner walls in pipelines, conduits, reaction vessels and similar process equipment, without chemically attacking or causing corrosion in the material which is used in such apparatuses.

According to one preferred embodiment of the present invention, the disinfectant also includes an additional chemical destruction agent of the above-described sporicidal, but corrosive type, such as peracetic acid, hydrogen peroxide, formaldehyde and glutaraldehyde. In such instance, it has surprisingly proved that the corrosive effect of such agents may be considerably reduced and even entirely eradicated while retaining sporicidal activity, even at very low concentrations of this agent. Such a "synergistic" effect is attained according to the present invention even at such low concentrations as between approx. 0.5 and 3.0 per cent which is the preferred concentration range for this agent when employed in the disinfectant according to the preferred embodiment of the invention.

Such a particularly preferred additional chemical destruction agent according to the invention is hydrogen peroxide in concentrations of between 0.5 and 3.0 per cent of the weight of a water-free alcohol solution.

Further advantageous and expedient embodiments of the disinfectant according to the present invention have moreover been given the characterising features as set forth in the appended subclaims.

The present invention will now be described in greater detail hereinbelow, with the aid of a non-restrictive practical embodiment in which the elimination efficiency of the disinfectant according to the present invention is illuminated.

To a water-free solution containing either propanol (n-propanol and/or isopropanol) or ethanol, hydrogen peroxide ($H_2O_2$) was added in quantities corresponding to between 0.5 and 3.0 per cent of the weight of the solution. A surface (metal, plastic) was inoculated with a hydrogen peroxide resistant spore suspension of *Bacillus subtilis* A (BSA 22), whereafter the inoculated surface was sprayed with a) water as control reference and b) one of the above-produced disinfectants according to the invention. After 15 min., the spore reduction effects of the different solutions (disinfectants) was determined by washing of the surfaces with swabs, preparation of test dilutions, and plating on PC agar.

The results showed that hydrogen peroxide in water had a very low reduction effect on the spores (within the range of 1 log) as compared with the control reference (the water), but that this effect increased within the concentration range of between 0.3 and 5.0 per cent. On the other hand, hydrogen peroxide in combination with the water-free solution of propanol (iso-propanol and/or n-propanol) or ethanol displayed a very good (synergistic) reduction effect between log 5 and log 6 with BSA spores in the concentration range of between 0.5 and 1.0 per cent.

It is thus apparent from the results of the described Example that the disinfectant according to the invention is a valuable chemical disinfectant possessing surprisingly good destruction effects also vis-a-vis spores. The disinfectant according to the present invention is particularly well-suited as bacteriological and sporicidal cleaning agent also in industrial contexts for cleaning surfaces of plastic, metal and rubber without corroding or otherwise attacking and destroying such surfaces. The disinfectant according to the invention is moreover easy to produce by a simple mixing process.

It should finally be observed that the above description is not intended to limit the present invention, various modifications and variations being possible without departing from the spirit and scope of the inventive concept as this is defined by the appended Claims. Such modifications and variations are, however, evident and obvious to a person skilled in the art and are thus intended to be encompassed by the scope of the appended Claims.

What is claimed is:

1. A method for disinfecting and cleaning equipment employed in industrial processes without chemically attacking or causing corrosion in said equipment, which comprises the step of contacting a surface of said equipment with a disinfectant comprising a practically water-free alcohol solution, hydrogen peroxide, wherein said hydrogen peroxide is present in a quantity of between 0.5 and 3.0% of the weight of said solution, and optionally a chemical destruction agent selected from the group consisting of peracetic acid, formaldehyde, and glutaraldehyde.

2. The method according to claim 1, wherein said surface is non-stainless steel, plastic, or rubber.

3. The method according to claim 1, wherein said hydrogen peroxide is present in a quantity of about 1% of the weight of said practically water-free alcohol solution.

4. The method according to claim 1, wherein said practically water-free alcohol solution is ethanol, n-propanol, or isoponanol, or mixtures thereof.

* * * * *